(12) United States Patent
Diener

(10) Patent No.: US 9,040,069 B2
(45) Date of Patent: May 26, 2015

(54) PROCESS FOR MANUFACTURING A STATIONARY STATE OF CRYSTALLINE POLYMER OF A BIODEGRADABLE POLYMER MATRIX CARRYING AN ACTIVE SUBSTANCE AND A POLYMER MATRIX PRODUCED THEREBY

(75) Inventor: Tobias Diener, Erlangen (DE)

(73) Assignee: BIOTRONIK VI Patent AG, Baar (CH)

( * ) Notice: Subject to any disclaimer, the term of this patent is extended or adjusted under 35 U.S.C. 154(b) by 1855 days.

(21) Appl. No.: 11/482,484

(22) Filed: Jul. 7, 2006

(65) Prior Publication Data

US 2008/0008735 A1    Jan. 10, 2008

(51) Int. Cl.
*A61L 31/10* (2006.01)
*A61L 31/16* (2006.01)

(52) U.S. Cl.
CPC .......... *A61L 31/16* (2013.01); *A61L 31/10* (2013.01); *A61L 2300/00* (2013.01)

(58) Field of Classification Search
None
See application file for complete search history.

(56) References Cited

U.S. PATENT DOCUMENTS

| 6,986,735 | B2 * | 1/2006 | Abraham et al. | 600/36 |
| 7,288,111 | B1 * | 10/2007 | Holloway et al. | 623/1.15 |
| 2003/0143315 | A1 * | 7/2003 | Pui et al. | 427/2.1 |
| 2003/0207856 | A1 * | 11/2003 | Tremble et al. | 514/183 |
| 2004/0034409 | A1 * | 2/2004 | Heublein et al. | 623/1.46 |
| 2004/0211362 | A1 * | 10/2004 | Castro et al. | 118/669 |
| 2004/0220665 | A1 * | 11/2004 | Hossainy et al. | 623/1.42 |
| 2004/0225350 | A1 * | 11/2004 | Shanley | 623/1.16 |
| 2005/0112170 | A1 * | 5/2005 | Hossainy et al. | 424/423 |
| 2006/0233850 | A1 * | 10/2006 | Michal | 424/422 |
| 2007/0026043 | A1 * | 2/2007 | Guan et al. | 424/426 |

FOREIGN PATENT DOCUMENTS

WO    WO 2005/004945 A2    1/2005

OTHER PUBLICATIONS

Ajioka et al. Journal of Environmental Polymer Degradation 1995 3:225-234.*
Porter et al. Journal of Thermal Analysis 1996 46:871-878.*
Mano et al. Polymer 2005 46:8258-8265.*
Sanchez et al. Biomacromolecules 2005 6:3283-3290.*

* cited by examiner

*Primary Examiner* — Robert A Wax
*Assistant Examiner* — Caralynne Helm
(74) *Attorney, Agent, or Firm* — Greer, Burns & Crain, Ltd.

(57) ABSTRACT

A method for manufacturing a stationary state of polymer crystallinity of an active substance charged polylactide matrix for a stent, comprising the steps of: preparing the active substance charged polylactide matrix containing (a) a polylactide in amorphous or semicrystalline modification or with amorphous domains, and (b) at least one active substance on a surface or in a cavity of the stent communicating with the surface; and heating of the active substance charged polylactide matrix to a temperature ranging from $T_G$-20° C. to $T_S$-10° C., where $T_G$ represents a glass transition temperature and $T_S$ a melting temperature of the crystallites of the polylactide.

18 Claims, 1 Drawing Sheet

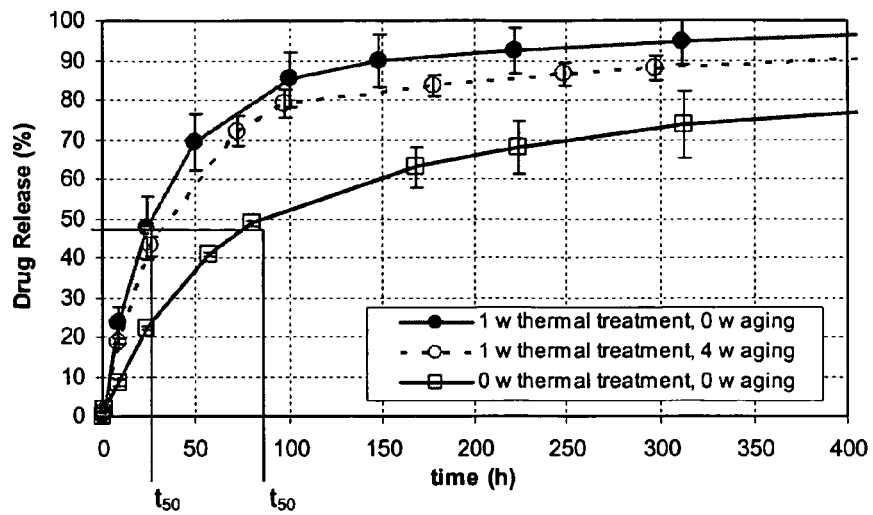
Fig. 1
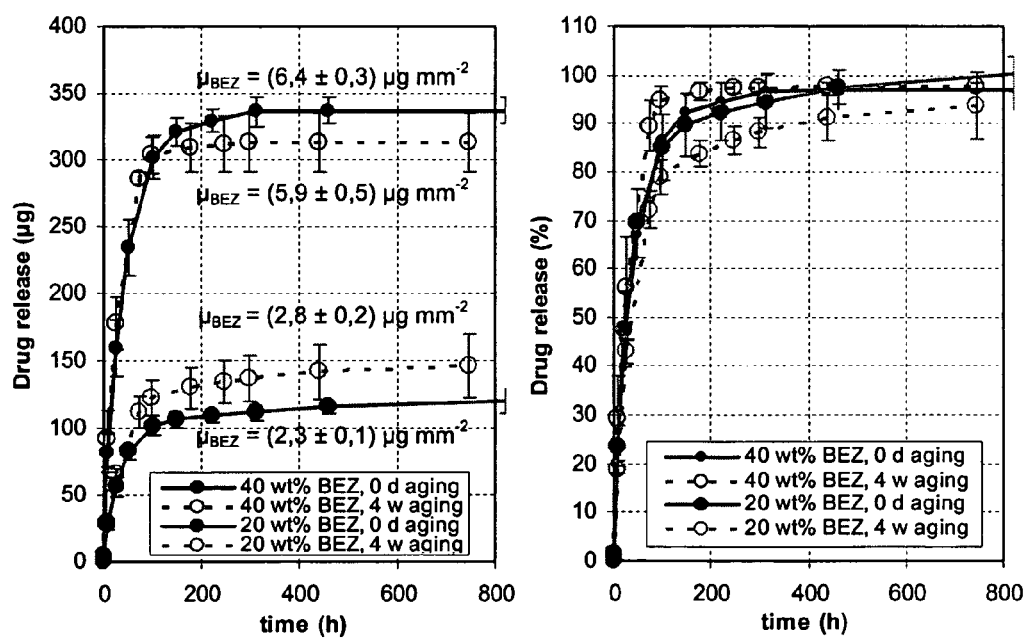
Fig. 2
Fig. 3

PROCESS FOR MANUFACTURING A STATIONARY STATE OF CRYSTALLINE POLYMER OF A BIODEGRADABLE POLYMER MATRIX CARRYING AN ACTIVE SUBSTANCE AND A POLYMER MATRIX PRODUCED THEREBY

FIELD OF THE INVENTION

The invention relates to a method for the manufacture of a stationary state of polymer crystallinity of an active substance charged biodegradable polylactide matrix, a polylactide matrix obtained according to the method and an implant with a coating from the polylactide matrix.

BACKGROUND OF THE INVENTION

Pharmaceutical active substances are frequently incorporated in a matrix formed from a biodegradable polymer for intracorporeal administration. The polymer matrix therefore represents an active substance depot (slow release) which is inserted/implanted in the body of the patient to be treated by surgery, and there gradually releases the active substance. The polymer matrix then degrades so that no further surgery is required for extraction of the polymer matrix. For example, the active substance charged polymer matrix may be introduced directly into the vascular system of a patient as an active substance depot or may be used to charge a cavity which forms part of the implant and from which the active substance is then released after implantation. Furthermore, the active substance charged polymer matrix may be applied to implants as a coating, e.g., heart pacemakers, defibrillators and stents, to assist in the healing process in the surrounding tissue and counteract tissue irritations caused by the release of active substances. Based on studies of the applicant it has proved particularly advantageous to use polylactides, particularly poly-L-lactides, as biodegradable polymers of the polymer matrix.

WO 2005/004945 discloses a method in which an active substance charged polymeric coating is heated on a stent for a predeterminable time above a glass transition temperature of the polymer in order to reduce the in vivo elution rate of an active substance. The experiments described relate only to the polymer ethylene vinyl alcohol copolymer (EVAL).

An essential criterion for suitability of polymer matrices for the release of active substances is, among other things, high reproducibility of the elution characteristic over time. However, studies of the applicant have shown that on a polylactide matrix the elution characteristic is dependent on the length of the storage time. In other words, the polylactide matrix ages after its manufacture, due mainly to crystallisation processes, and this morphological change influences the elution of the active ingredient. Consequently, measures would be required to stabilise the elution characteristic during the storage period. However, of the active substance from the polylactide matrix should in this case not be reduced but increased further, if possible.

SUMMARY OF THE INVENTION

The one feature of this invention is therefore to provide a method with which the above-mentioned disadvantages of the state of the art can be overcome and improved storage stability of the polylactide matrix can be achieved in terms of its elution characteristic.

According to one aspect of the invention this feature is achieved by providing a method for manufacturing a stationary state of polymer crystallinity of an active substance charged polylactide matrix for a stent. The method according to the invention comprises the following steps:

(i) preparation of the active substance charged polylactide matrix containing (a) a polylactide in amorphous or semi-crystalline modification, or with amorphous domains, and (b) at least one active substance on a surface or in a cavity of the stent connected to the surface; and (ii) heating of the active substance charged polylactide matrix to a temperature ranging from $T_G$-20° C. to $T_S$-10° C., where $T_G$ represents a glass transition temperature and $T_S$ a melting temperature of the crystallites of the polylactide.

The invention is based on the knowledge that tempering the active substance charged polylactide matrix within the temperature limits mentioned eliminates the risk of the recrystallisation of frozen, crystallisable amorphous polymer domains of the polymer matrix. In other words, a stationary state of polymer crystallinity is produced by tempering without this resulting in thermal degradation of the polymer matrix. Our own studies have shown that a suitably tempered polymer matrix is storage stable in terms of its elution characteristic, i.e., the elution characteristic was disassociated from the phenomenon of recrystallisation of frozen, crystallisable amorphous polymer domains.

Surprisingly it has been shown that the tempering according to the invention also results in an acceleration of the active substance elution, which is advantageous when combined with stent coating systems, because in this application a locally high active substance dose immediately after implantation is desirable. Normally an inhibition of the diffusive processes, or a deceleration in active substance elusion might be expected as the crystallinity of the matrix increases, as also described for example in WO 2005/004945. The opposite effect of accelerated release now established is probably due to the active substance enrichment on the crystalline polymer domains additionally produced by tempering. This phase segregation results in increased active substance concentration in the amorphous domains of the polylactide matrix compared to its crystalline domains.

It has also been shown that the storage stability achieved by the tempering according to the invention is independent of the level of charging of the polylactide matrix with the active substance. Tests with different proportions of an active substance by weight therefore showed that up to a certain time the same quantities of active substances are released and that the differences in the curve observed after that time are due to the differences in active substance charging, i.e., the different plateau values.

The manufacture of a stationary state of polymer crystallinity, within the meaning of the present invention, is understood to refer to the attainment of a modification of the polymers, where a proportion of the amorphous polymer domains that can be crystallised at room temperature is less than 10% by weight, in particular less than 5% by weight of the total weight of the polylactide (not charged with active substance). Storage stability within the meaning of the invention is therefore a state in which the elution characteristic during the storage time, normally a period ranging from several days to several months, shows at least slight deviations over time.

A polylactide that can be used for the purposes of the invention is characterised in that after the active substance charged polylactide matrix is manufactured the polylactide is present in whole or at least in parts in an amorphous modification. Furthermore, the polymer modification is such that recrystallisation would take place over time under the conditions of normal storage, particularly to an extent of >5% by weight of the total weight of the polylactide (not charged with active substance).

The glass transition temperature $T_G$ (also called softening temperature) is the temperature at which an amorphous polylactide shows the greatest change in deformability and this so-called glass transition separates the brittle energy-elastic domain below from the soft entropy-elastic domain above. Partially crystalline polylactides have both a glass transition temperature $T_G$, at which the amorphous phase decomposes, and a melting temperature $T_S$, at which the crystalline phase dissolves. The melting temperature $T_S$ separates the entropy-elastic domain clearly from the flow domain. The glass transition temperature $T_o$ can be measured by means of dynamic-mechanical analysis or dynamic differential calorimetry. In step (ii) of the method the temperature should preferably range from $T_G$-20° C. to $T_S$-10° C., in order to minimise the risk of thermal damage to the active substance charged polylactide matrix. Since the mobility of the chain segments increases in the region of the glass transition temperature $T_G$, tempering may also be carried out just below this temperature. The following applies: the higher the temperature the shorter will be the tempering time, but this may increase the extent of the thermally induced damage to the polymer.

According to a preferred variant the biodegradable polylactide poly-L-lactide is used. The tempering in step (ii) preferably takes place here at a temperature ranging from 45-55° C., in particular at approximately 50° C. Surprisingly it has been shown that a molecular weight of the poly-L-lactide carrier matrix within a wide molecular weight range from 73.000 g/mol to 690.000 g/mol has no influence on the elution rate of incorporated drugs.

The active substance charged polylactide matrix contains the biodegradable polylactide and at least one active substance. In other words, the addition of further additives or fillers is conceivable, e.g., in order to influence the crystallinity of the polymer matrix.

Active substances within the meaning of the present invention are vegetable, animal or synthesised substances which are used for diagnosis or, in a suitable dose, as therapeutics for influencing conditions or functions of the body, as a substitute for active substances produced naturally by the human or animal body, and for removing or rendering harmless pathogens, parasites or foreign substances. Preferably the active substance is bezafibrate.

Another method variant which can also be carried out in conjunction with the previously mentioned preferred variant of the invention provides that the preparation of the polylactide matrix according to step (i) is carried out by applying a finely dispersed aerosol to a surface of a stent by means of a rotary atomiser. Homogeneous coatings can be produced extremely easily by this method. Preferably the average droplet size of the aerosol in this case is <70 μm, and in particular in the range of 5 to 25 μm. This avoids adhesion of the individual stent struts.

Using mathematical methods it is possible to determine the dimension or design characteristics of the atomisers to be used so that speed and volumetric flow, for example, can be calculated beforehand. In addition to the polymer and active substance properties, the thickness of the polylactide coat is also a determining factor for the elution characteristic. The reservoir volume of the active substance can be set with variable coat thicknesses. Both the elution rate and the duration of active substance release can be set on the basis of engineering/technical parameters such as the degree of charging and reservoir volume, and the application of an active substance free top coat.

The coat thickness of a coating applied as an aerosol preferably lies within the range of 3-7 m on the lumen side; preferably, this coat thickness is approximately 5 μm. This ensures that where there is no covalent connection of the coating to the base body of the implant, the positive closure required for adhesion is maintained, but without any disturbing contraction of the inner lumen of the implant.

A second aspect of the invention lies in the preparation of a stent with a polylactide matrix which can be manufactured by the method previously described. The tempering results in a modification change in the active substance charged polylactide matrix, which is demonstrable in the product and ultimately improves storage stability and reduces variance in the elution characteristic.

BRIEF DESCRIPTION OF THE DRAWINGS

The invention is explained in greater detail in the following with reference to exemplary embodiments and associated drawings:

FIG. 1 shows an application of the active substance composition of 20% by weight of bezafibrate-charged stents after sterilisation (E-Beam, 25 kGy), without subsequent tempering, with tempering (1 week, 50° C.) and with tempering followed by aging (4 weeks, room temperature); elution medium: Porcines Plasma, 37°;

FIG. 2 shows an application of the active substance recovery of 20% by weight of bezafibrate-charged stents after sterilisation (E-Beam, 25 kGy) and tempering (1 week, 50° C.) with and without subsequent aging (4 weeks, room temperature); elution medium: Porcines Plasma, 37° C., statistics per n=3; and, FIG. 3 shows an application of the eluted active stance mass of 20% by weight and 40% by weight of bezafibrate-charged stents after sterilisation (E-Beam, 25 kGy) and tempering (1 week, 50° C.), with and without subsequent aging (4 weeks, room temperature); elution medium: Porcines plasma, 37° C., statistics per n=3.

DETAILED DESCRIPTION OF THE INVENTION AND EXAMPLES

A stent of medical steel was coated by means of a rotary atomiser as follows:

The material properties for poly-L-lactide are known from the relevant literature and shown in Table 1:

TABLE 1

| Property | | Poly-L-lactide |
|---|---|---|
| Proportions D, L/L | [mol %] | 100/0 |
| Degree of crystallinity $\square$ | [%] | <80 |
| Glass transition temperature $T_G$ | [° C.] | 60-70 |
| Melting temperature $T_S$ | [° C.] | 170-180 |
| Molecular weight $M_w$ | [g/mol] | <2.000.000 |
| Solvent | | $CHCl_3$, $CH_3Cl$ |
| Density $\square_{amorph}/\square_{crystalline}$ | [g/cm$^3$] | 1.25-1.29/~1.45 |
| Modulus of elasticity $E^{l)}$ | [N/mm$^2$] | <5.000 |
| Tensile strength $\square_b{}^{l)}$ | [N/mm$^2$] | <72 |
| Bending strength $\square_b{}^{l)}$ | [N/mm$^2$] | <145 |
| Elongation at rupture $\square^{l)}$ | [%] | <6.0 |

The poly-L-lactides used, from Boehringer-Ingelheim, Germany, have the specific material properties indicated in Table 2:

TABLE 2

| Specification | | L210 | L214 |
|---|---|---|---|
| Composition L/D, L | [mol %] | 100/0 | |
| Solubility | | Chloroform, methyl chloride | |
| Residual content of monomer/solvent | [%] | ≤0.1/≤0.089 | |
| Metal residues tin/other | [ppm] | ≤100/≤10 | |
| Water content/sulphur content | [%] | ≤0.5/≤0.1 | |
| Inherent viscosity | [dl/g] | 2.8 | 8.0 |
| Molecular weight $M_w$ (GPC/MHE) | [kg mol$^{-1}$] | 680/305 | 1.702/691 |
| Inhomogeneity $U = [(M_w/M_n) - 1]$ | [—] | 0.57 | 0.63 |

Bezafibrate, from Heumann, Germany, belongs to the substance class of fibrates which, because of their inhibiting action on the biosynthesis of cholesterol, may be classified in the lipid reducer group, and is ideal for use as a therapeutic for optimum healing of the stented vessel.

Because of their dose-dependent inhibition of the interleukin-6 (IL-6) release, fibrates reduce the inflammatory processes in the artery wall. Moreover, they reduce the blood fat values, particularly the triglyceride and cholesterol level, and are used accordingly for treating hyperglyceridaemia and hypercholesterolaemia respectively. Among other things, the fibrates belong to the so-called peroxisomic proliferators (PP's), since they induce the propagation of peroxisomes (cell organels). They exert their action by activating intracellular receptors, the peroxisome proliferators activated receptors (PPAR's). The PPAR's are specific ligand activated transcription factors. Activated agonist receptor complexes reach the cell nucleus in order to stimulate the expression of certain genes. In tissues outside the liver PP's have demonstrated a partial anti-tumorigenic action. Conventional stents from the material L215 have been used.

Agitating with a magnetic agitator (6h), a solution of 7.5 g poly-L-lactide was added to 1 l of chloroform. Two aerosol master solutions were manufactured from this solution by splitting and the addition of bezafibrate, the solutions containing (a) 20% by weight of bezafibrate and (b) 40% by weight of bezafibrate, elated in each case to the quantity of poly-L-lactide in these master solutions.

The stents were clamped in a conventional rotary atomiser and coated with the master aerosol solutions (a) and (b), the droplet size of the aerosol being approximately 15 μm. The light microscopic assessment of the coated stents did not show major polymer accumulations in the bends of the stent until below a radius of 50 μm and until individual struts showed adhesions below a strut to strut distance of approximately 80 μm.

A positive coating was carried out to counteract detachment of the coat from the substrate under tribological loads, e.g., during transition through stenosis and during later dilation. In addition to the positive closure of the coating, required to guarantee mechanical stability, the homogeneity of the coat applied was also determined from cross-sections along individual stent segments.

On the vessel side, i.e., on the outside of the stent, the coat thickness was approximately 19 μm. The thickness of the manufactured drug incorporated polymer coat on the lumen side was approximately 5 μm.

The presence of a locally homogeneous active substance elution was demonstrated by examination, segment by segment, of the active substance charge by solid phase extraction.

FIG. 1 shows an application of the active substance composition of bezafibrate-charged stents after sterilisation (E-Beam, 25 kGy) without subsequent tempering, with tempering (1 week, 50° C.) and with tempering with subsequent aging (4 weeks, room temperature)—always in the Porcines Plasma at 37° C. It is clear from the course of the curves that tempering at 50° C. over one week results in a stationary state of polymer crystallinity, where there is no longer any recrystallisation of frozen, crystallisable amorphous polymer domains.

The associated morphological change influences the elution behaviour of the incorporated active substance: the untempered stents, not subject to additional aging, have a comparatively slow elution characteristic, with a half life (in vitro test time for 50% active substance elution) of $t_{50}$=87.2 h, whilst the $t_{50}$ value reduced by 70% to 26.5 h in the case of the tempered stents. Normally inhibition of the diffuse processes and a deceleration of the active substance elution would be expected with increasing crystallinity of the matrix. This effect would be caused by recrystallisation during tempering due to the low available free volume of the polymer clusters and reduced mobility of polymer segments. The opposite effect of accelerated release now detectable in the elution curves could be due to active substance enrichment in the crystalline polymer domains. The phase segregation that takes place due to the temperature-indicated recrystallisation was determined with DSC analyses with reference to a splitting of the melting peak into two discrete individual peaks. The higher active substance concentration thus caused in the amorphous domains of the poly-L-lactide therefore also gives rise to a faster active substance elution compared to its crystalline domains.

The in vitro analysis of stents that have been temperature treated, then stored for 4 weeks under normal conditions, shows no significant variation in the elution characteristic, within the standard deviation, compared to tempered and non-aged stents.

The storage stability achieved by tempering is also independent of the level of charging of the polylactide matrix with the active substance, as shown in FIGS. 2 and 3 taking the example of 20% by weight and 40% by weight of bezafibrate-charged polymer matrices. Up to a 50 h test time of those charged with 20% by weight, and up to 100 h with an active substance proportion of 40% by weight, the same quantities of active substances are released from the aged and non-aged stents, and it is only after these times that the curve courses change. However, their different values are due solely to the differences in active substance charges $\mu_{BEZ}$, as can also be deduced from the size of the error bars correlated with the tolerances of the active substance charge. The same elution kinetics for all stents is evident from the standardised application of the eluted active substance proportions within the limits of test accuracy.

It should be noted that the active substance charged poly-L-lactide polymer matrix remained stable under the test conditions, in other words it was not subject to thermally induced degradation.

The invention claimed is:

1. A method for manufacturing a storage stable stationary state of polymer crystallinity of an active substance charged polylactide matrix for a stent, the method comprising:

(i) preparing the active substance charged polylactide matrix containing, (a) a semicrystalline polylactide, wherein the polylactide has a glass transition temperature $T_G$ of from 60-70° C. and a melting temperature $T_S$ of from 170-180° C., with an average $T_G$ and $T_S$, ($T_G$+$T_S$/2) of 115° C. to 125° C., where $T_G$ represents a glass transition temperature and $T_S$ a melting temperature of the crystallites of the polylactide, and (b) at least one active substance, wherein the active substance charged polylactide matrix is on a surface or in a cavity of the stent communicating with the surface; and (ii) heating the active substance charged polylactide matrix to a temperature ranging from 45° C. to 55° C. for one week to form the storage stable stationary state of polymer crystallinity of the active substance charged polylactide matrix containing less than 10% by weight of amorphous polymer domains that can be crystallized at room temperature based on the total weight of polylactide.

2. The method of claim 1, wherein the polylactide is a poly-L-lactide.

3. The method of claim 1, wherein step (i) is carried out by applying a finely dispersed aerosol to a surface of the stent by means of a rotary atomiser.

4. The method of claim 3, wherein the aerosol has an average droplet size of <70 μm.

5. The method of claim 3, wherein the aerosol is applied so as to apply a coating having a thickness on the lumen side in a range of about 3-7 μm.

6. The method of claim 1 wherein the active substance is a fibrate.

7. The method of claim 6 wherein the fibrate is a lipid reducer group fibrate.

8. The method of claim 7 wherein the lipid reducer group fibrate is bezafibrate.

9. The method of claim 1 wherein the storage stability is independent of the level of the active substance charged in the active substance charged polylactide matrix.

10. The method of claim 1 wherein the active substance elution is increased compared to the active substance elution of the active substance charged polylactide matrix without heating.

11. A stent with a polylactide matrix according to claim 1.

12. A method for manufacturing a storage stable stationary state of polymer crystallinity of an active substance charged polylactide matrix for a stent, the method comprising:

(i) preparing the active substance charged polylactide matrix containing,
  (a) a semicrystalline polylactide, wherein the polylactide has a glass transition temperature $T_G$ of from 60-70° C. and a melting temperature $T_S$ of from 170-180° C., with an average $T_G$ and $T_S$, $(T_G+T_S/2)$ of 115° C. to 125° C., where $T_G$ represents a glass transition temperature and $T_S$ a melting temperature of the crystallites of the polylactide, and
  (b) at least one active substance, wherein the active substance charged polylactide matrix is on a surface or in a cavity of the stent communicating with the surface; and (ii) heating the active substance charged polylactide matrix to a temperature ranging from 45° C. to 55° C. for one week to form the storage stable stationary state of polymer crystallinity of the active substance charged polylactide matrix containing less than 10% by weight of amorphous polymer domains that can be crystallized at room temperature based on the total weight of polylactide, and wherein an active substance elution is increased compared to an active substance elution of a polylactide matrix without heating.

13. The method of claim 12, wherein the polylactide is a poly-L-lactide.

14. The method of claim 12, wherein step (i) is carried out by applying a finely dispersed aerosol to a surface of the stent by means of a rotary atomiser, and wherein the aerosol has an average droplet size of <70 μm.

15. The method of claim 14, wherein the aerosol is applied so as to apply a coating having a thickness on the lumen side in a range of about 3-7 μm.

16. The method of claim 12 wherein the active substance is a fibrate.

17. The method claim 16 wherein the fibrate is benzfibrate.

18. The method of claim 12 wherein the storage stability is independent of the level of the active substance charged in the active substance charged polylactide matrix.

* * * * *